(12) United States Patent
Pianca et al.

(10) Patent No.: US 8,831,742 B2
(45) Date of Patent: Sep. 9, 2014

(54) SYSTEMS AND METHODS FOR IDENTIFYING THE CIRCUMFERENTIAL POSITIONING OF ELECTRODES OF LEADS FOR ELECTRICAL STIMULATION SYSTEMS

(71) Applicant: Boston Scientific Neuromodulation Corporation, Valencia, CA (US)

(72) Inventors: Anne Margaret Pianca, Santa Monica, CA (US); Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/750,725

(22) Filed: Jan. 25, 2013

(65) Prior Publication Data

US 2013/0197602 A1    Aug. 1, 2013

Related U.S. Application Data

(60) Provisional application No. 61/591,046, filed on Jan. 26, 2012.

(51) Int. Cl.
| | |
|---|---|
| *A61N 1/04* | (2006.01) |
| *H01R 43/16* | (2006.01) |
| *A61N 1/36* | (2006.01) |
| *A61N 1/05* | (2006.01) |

(52) U.S. Cl.
CPC .............. *A61N 1/0534* (2013.01); *H01R 43/16* (2013.01); *A61N 1/3606* (2013.01)
USPC ....................................................... 607/116

(58) Field of Classification Search
None
See application file for complete search history.

(56) References Cited

U.S. PATENT DOCUMENTS

| | | | |
|---|---|---|---|
| 4,602,624 | A | 7/1986 | Naples et al. |
| 4,630,611 | A | 12/1986 | King |
| 4,744,370 | A | 5/1988 | Harris |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

U.S. Appl. No. 12/177,823, filed Jul. 22, 2008.

(Continued)

*Primary Examiner* — Brian T Gedeon
(74) *Attorney, Agent, or Firm* — Lowe Graham Jones PLLC; Patrick R. Turner

(57) ABSTRACT

A lead assembly for an electrical stimulation system includes terminals disposed along a proximal end of a lead body and electrodes disposed along a distal end of the lead body. The electrodes include segmented electrodes. At least one distal marker is disposed along the distal end of the lead body. The distal marker identifies the circumferential position of at least one of the segmented electrodes along the lead body. The distal marker is aligned with at least one of the segmented electrodes along the longitudinal length of the lead body. At least one proximal marker is disposed along the proximal end of the lead body. The proximal marker is aligned with the distal marker along the longitudinal length of the lead body. The distal marker and the proximal marker are discontinuous with one another along the lead body.

20 Claims, 6 Drawing Sheets

(56) References Cited

U.S. PATENT DOCUMENTS

| | | | |
|---|---|---|---|
| 5,000,194 A | 3/1991 | van den Honert et al. | |
| 5,135,001 A | 8/1992 | Sinofsky et al. | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,134,478 A | 10/2000 | Spehr | |
| 6,161,047 A | 12/2000 | King et al. | |
| 6,167,311 A | 12/2000 | Rezai | |
| 6,249,708 B1 * | 6/2001 | Nelson et al. | 607/122 |
| 6,322,559 B1 | 11/2001 | Daulton et al. | |
| 6,510,347 B2 | 1/2003 | Borkan | |
| 6,556,873 B1 | 4/2003 | Smits | |
| 6,564,078 B1 | 5/2003 | Marino et al. | |
| 6,678,564 B2 | 1/2004 | Ketterl et al. | |
| 6,757,970 B1 | 7/2004 | Kuzma et al. | |
| 7,027,852 B2 | 4/2006 | Helland | |
| 7,047,084 B2 | 5/2006 | Erickson et al. | |
| 7,292,890 B2 | 11/2007 | Whitehurst et al. | |
| 7,395,116 B2 * | 7/2008 | Mehdizadeh et al. | 607/37 |
| 7,489,971 B1 | 2/2009 | Franz | |
| 7,668,601 B2 | 2/2010 | Hegland et al. | |
| 7,761,985 B2 | 7/2010 | Hegland et al. | |
| 7,809,446 B2 | 10/2010 | Meadows | |
| 7,840,188 B2 | 11/2010 | Kurokawa | |
| 7,848,802 B2 * | 12/2010 | Goetz et al. | 607/2 |
| 7,856,707 B2 | 12/2010 | Cole | |
| 7,860,570 B2 | 12/2010 | Whitehurst et al. | |
| 7,974,705 B2 | 7/2011 | Zdeblick et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,099,177 B2 | 1/2012 | Dahlberg | |
| 8,225,504 B2 | 7/2012 | Dye et al. | |
| 8,295,944 B2 | 10/2012 | Howard et al. | |
| 8,321,025 B2 | 11/2012 | Bedenbaugh | |
| 8,473,074 B2 * | 6/2013 | North et al. | 607/116 |
| 8,560,085 B2 | 10/2013 | Moffitt et al. | |
| 8,583,237 B2 | 11/2013 | Bedenbaugh | |
| 8,649,879 B2 | 2/2014 | DiGiore et al. | |
| 2002/0156513 A1 | 10/2002 | Borkan | |
| 2002/0183817 A1 | 12/2002 | Van Venrooij et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0247697 A1 | 11/2006 | Sharma et al. | |
| 2007/0150036 A1 | 6/2007 | Anderson | |
| 2007/0203546 A1 | 8/2007 | Stone et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2009/0187222 A1 | 7/2009 | Barker | |
| 2009/0204192 A1 | 8/2009 | Carlton et al. | |
| 2009/0276021 A1 | 11/2009 | Meadows et al. | |
| 2010/0036468 A1 | 2/2010 | Decre et al. | |
| 2010/0076535 A1 | 3/2010 | Pianca et al. | |
| 2010/0082076 A1 | 4/2010 | Lee et al. | |
| 2010/0094387 A1 | 4/2010 | Pianca et al. | |
| 2010/0268298 A1 | 10/2010 | Moffitt et al. | |
| 2011/0005069 A1 | 1/2011 | Pianca | |
| 2011/0047795 A1 | 3/2011 | Turner et al. | |
| 2011/0056076 A1 | 3/2011 | Hegland et al. | |
| 2011/0078900 A1 | 4/2011 | Pianca et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0131808 A1 | 6/2011 | Gill | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | DiGiore et al. | |
| 2012/0203321 A1 | 8/2012 | Moffitt et al. | |
| 2013/0197424 A1 | 8/2013 | Bedenbaugh | |
| 2013/0197602 A1 | 8/2013 | Pianca | |
| 2013/0317587 A1 | 11/2013 | Barker | |
| 2013/0325091 A1 | 12/2013 | Pianca | |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009025816 A1 | 2/2009 |
| WO | 2009102536 A1 | 8/2009 |
| WO | 2012109338 A2 | 8/2012 |

OTHER PUBLICATIONS

U.S. Appl. No. 61/170,037, filed Apr. 16, 2009.
U.S. Appl. No. 61/022,953, filed Jan. 23, 2008.
U.S. Appl. No. 61/316,759, filed Mar. 23, 2010.
U.S. Appl. No. 61,494,247, filed Jun. 7, 2011.
U.S. Appl. No. 61/554,861, filed Nov. 2, 2011.
U.S. Appl. No. 61/364,960, filed Jul. 16, 2010.
International Search Report and Written Opinion for International Patent Application No. PCT/US2013/023248 mailed Apr. 3, 2013.
U.S. Appl. No. 13/787,171, filed Mar. 6, 2013.
U.S. Appl. No. 13/951,057, filed Jul. 25, 2013.
U.S. Appl. No. 14/053,112, filed Oct. 14, 2013.
U.S. Appl. No. 14/173,593, filed Feb. 5, 2014.
U.S. Appl. No. 14/189,671, filed Feb. 25, 2014.

* cited by examiner

SYSTEMS AND METHODS FOR IDENTIFYING THE CIRCUMFERENTIAL POSITIONING OF ELECTRODES OF LEADS FOR ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/591,046 filed on Jan. 26, 2012, which is incorporated herein by reference.

FIELD

The invention is directed to the area of electrical stimulation systems and methods of making and using the systems. The present invention is also directed to electrical stimulation leads having electrodes and markers identifying the circumferential positioning of one or more of the electrodes, as well as methods of making and using the leads, electrodes, markers, and electrical stimulation systems.

BACKGROUND

Electrical Stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

In one embodiment, a lead assembly for an electrical stimulation system includes a lead body having a distal end, a proximal end, a longitudinal length, and a circumference. A plurality of electrodes are disposed along the distal end of the lead body. The plurality of electrodes include a plurality of segmented electrodes. Each of the plurality of segmented electrodes extends partially around the circumference of the lead body. A plurality of terminals are disposed along the proximal end of the lead body. A plurality of conductors electrically couple at least one of the plurality of electrodes to at least one of the plurality of lead terminals. At least one distal marker is disposed along the distal end of the lead body. The distal marker identifies the circumferential position of at least one of the plurality of segmented electrodes along the lead body. The distal marker is aligned with the at least one of the plurality of segmented electrodes along the longitudinal length of the lead body. At least one proximal marker is disposed along the proximal end of the lead body. The proximal marker is aligned with the distal marker along the longitudinal length of the lead body. The at least one distal marker and the at least one proximal marker are discontinuous with one another along the lead body.

In another embodiment, a method for marking a lead of an implantable electrical stimulation system includes forming an elongated multi-lumen conductor guide defining a central lumen and a plurality of conductor lumens arranged around the central lumen. At least a portion of the multi-lumen conductor guide is twisted to form at least one helical section where the plurality of conductor lumens each forms a helical pathway around the central lumen. At least one conductor is inserted into one of the plurality of conductor lumens. A plurality of segmented electrodes are formed along one end of the multi-lumen conductor guide. The plurality of segmented electrodes are electrically coupled to the at least one conductor. An ablation is formed along a longitudinal length of the twisted multi-lumen conductor guide. The ablation is aligned along the longitudinal length of the multi-lumen conductor guide with a one of the plurality of segmented electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and methods of making and using the systems. The present invention is also directed to electrical stimulation leads having electrodes and markers identifying the circumferential positioning of one or more of the electrodes, as well as methods of making and using the leads, electrodes, markers, and electrical stimulation systems.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Pat. No. 7,809,446 ("Devices and Methods For Brain Stimulation"), U.S. Patent Application Publication No. 2010/0076535 A1 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. Patent Application Publication No. 2009/0276021 A1 ("Electrodes For Stimulation Leads and Methods of Manufacture and Use"), U.S. Patent Application Ser. No. 61/170,037 ("Deep Brain Stimulation Current Steering with Split Electrodes"), U.S. Patent Application Ser. No. 61/022,953, U.S. Patent Application Ser. No. 61/316,759, and U.S. Patent Application Publication No. 2009/0187222 A1. Each of these references is incorporated herein by reference in its respective entirety.

Figure 1:
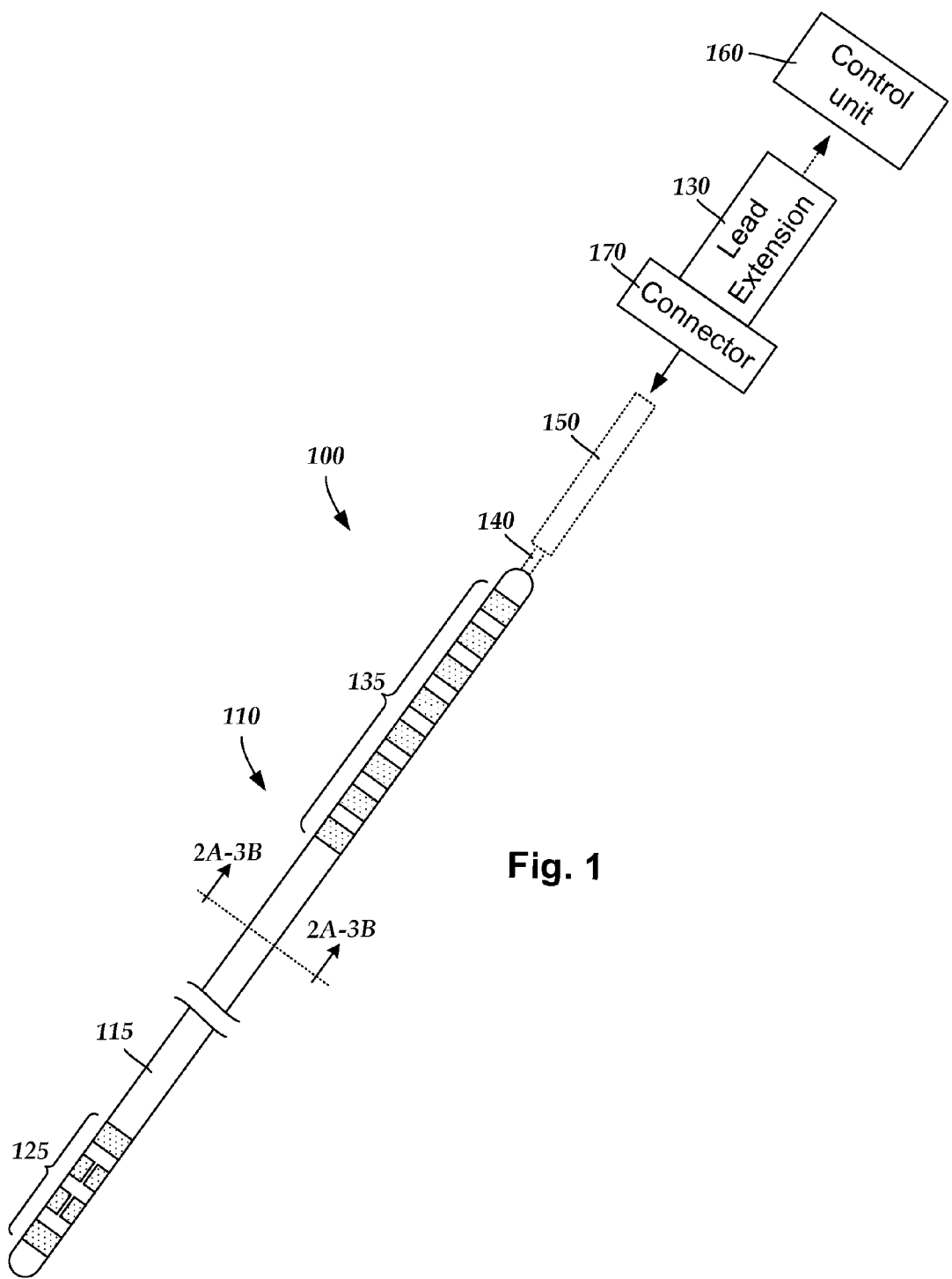
FIG. 1 is a schematic side view of one embodiment of a brain stimulation system that includes a lead with a lead body, a lead extension, and a control unit, according to the invention.

FIG. 1 illustrates one embodiment of an electrical stimulation system 100 for brain stimulation. The electrical stimulation system 100 includes a lead 110 having a lead body 115, a plurality of electrodes 125 disposed at least partially about a circumference of the lead body 115, a plurality of terminals 135, a lead extension 130 for connection of the electrodes 125 to a control unit 160, and a stylet 140 for assisting in insertion and positioning of the lead 110 in the patient's brain. It may be advantageous to include the lead extensions 130 to prevent having to remove or replace the lead 110 if the proximal end of the lead 110 fails due to fatigue (e.g., from flexing of the patient's neck, or the like).

The stylet 140 can be made of a rigid material. Examples of suitable materials include tungsten, stainless steel, or plastic. The stylet 140 may have a handle 150 to assist insertion into the lead 110, as well as rotation of the stylet 140 and lead 110. The lead extension 130 includes a connector 170 that fits over a proximal end of the lead 110, preferably after removal of the stylet 140.

The control unit 160 is typically an implantable pulse generator that can be implanted into a patient's body, for example, below the patient's clavicle area. The pulse generator can have eight stimulation channels which may be independently programmable to control the magnitude of the current stimulus from each channel. In some cases, the pulse generator may have more than eight stimulation channels (e.g., 16-, 32-, or more stimulation channels). The control unit 160 may have one, two, three, four, or more connector ports, for receiving the plurality of terminals 135 at the proximal end of the lead 110.

In one example of operation, access to the desired stimulation location in the brain can be accomplished by drilling a hole in the patient's skull or cranium with a cranial drill (commonly referred to as a "burr" or "bur"), and coagulating and incising the dura mater, or brain covering. The lead 110 can be inserted into the cranium and brain tissue with the assistance of the stylet 140. The lead 110 can be guided to the target stimulation location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 has a cross-sectional diameter of no more than 1.5 mm and may be in the range of no less than 0.5 mm and no greater than 1.5 mm. In at least some embodiments, the lead 110 is rotatable so that the stimulation electrodes 125 can be aligned with the target neurons after the neurons have been located using the recording electrodes. The stimulation electrodes 125 may be disposed on the circumference of the lead 110 to stimulate the target neurons. The stimulation electrodes 125 may be ring-shaped so that current projects from each electrode equally in every direction at any given length along the axis of the lead. To achieve current steering, segmented electrodes can be utilized additionally or alternatively. Though the following description discusses stimulation electrodes, it will be understood that all configurations of the stimulation electrodes discussed may be utilized in arranging recording electrodes as well.

The stimulation electrodes 125 may be made using a metal, alloy, conductive oxide, or any other suitable conductive material. Examples of suitable materials include, but are not limited to, platinum, platinum iridium alloy, palladium, palladium-rhodium alloy, or titanium. Preferably, the stimulation electrodes 125 are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a first period of time and a cathode for a second, non-overlapping period of time. In other embodiments, the identity of a particular electrode or electrodes as an anode or cathode might be fixed.

The lead extension 130 typically couples the electrodes 125 to the control unit 160 (which typically houses a pulse generator that supplies electrical signals to the electrodes 125). Connectors of conventional lead extensions are typically disposed within patient tissue such that the connectors are disposed over the patient's skull and beneath or within the patient's scalp above one of the patient's ear.

Turning to FIGS. 2A-3B, in at least some embodiments the lead body 115 may include strain relief to modulate deflection of one or more portions of the lead in response to bending of one or more portions of the lead. Examples of lead bodies with strain relief are found in, for example, U.S. Patent Application Ser. No. 61/494,247 and U.S. Patent Application Ser. No. 61/554,861, each of which is incorporated herein by reference in its entirety. Strain relief may be provided in any suitable manner. In some embodiments, the lead includes a lead body with one or more elongated multi-lumen conductor guides. In which case, the one or more multi-lumen conductor guides may include conductor lumens with one or more helical sections that provide strain relief.

In at least some embodiments, the lead body 115 includes an elongated multi-lumen conductor guide having multiple conductor lumens arranged about a central lumen. In at least some embodiments, the conductor lumens are arranged about the central lumen such that there are no other lumens extending along the multi-lumen conductor guide between the central lumen and each of the multiple conductor lumens. The conductor lumens include at least one helical section forming an enclosed pathway around at least a portion of the central lumen. In some embodiments, the conductor lumens are each configured and arranged to receive a single conductor. In other embodiments, at least one of the conductor lumens is configured and arranged to receive multiple conductors.

Figure 2A:
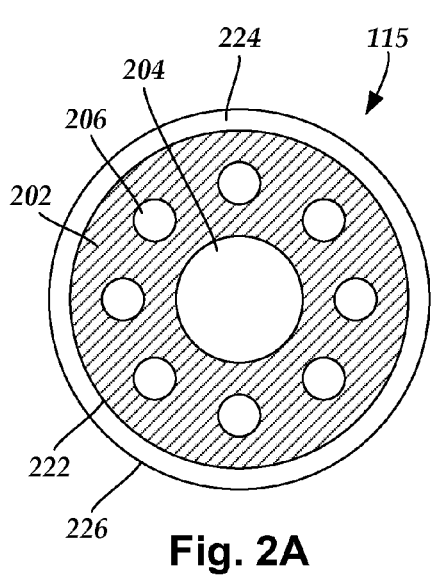
FIG. 2A is a transverse cross-sectional view of one embodiment of a portion of the lead body of FIG. 1, the lead body including a multi-lumen conductor guide that defines a central lumen and a plurality of conductor lumens arranged around the central lumen, according to the invention.

FIG. 2A is a transverse cross-sectional view of one embodiment of a portion of the lead body 115. The lead body 115 includes an elongated multi-lumen conductor guide 202 defining a central lumen 204 and a plurality of conductor lumens, such as conductor lumen 206, disposed around the central lumen 204. The central lumen 204 may be configured and arranged to receive a stylet, such as the stylet (140 in FIG. 1). As discussed above, the stylet 140 can be used for assisting in insertion and positioning of the lead in the patient's brain.

Figure 2B:
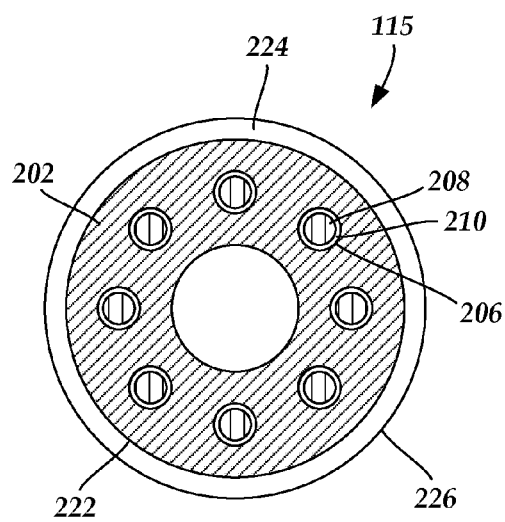
FIG. 2B is a transverse cross-sectional view of one embodiment of conductors disposed in each of a plurality of conductor lumens of the multi-lumen conductor guide of FIG. 2A, according to the invention.

FIG. 2B is a transverse cross-sectional view of one embodiment of conductors, such as conductor 208, disposed in conductor lumens 206. In at least some embodiments, insulation 210 is disposed around the conductors 208 to prevent short-circuiting of the conductors 208. The multi-lumen conductor guide 202 may extend an entire longitudinal length of the lead body 115 from the electrodes 125 to the terminals 135. The conductor lumens 206 can have any suitable cross-sectional shape (e.g., round, oval, rectangular, triangular, or the like).

Figure 3A:
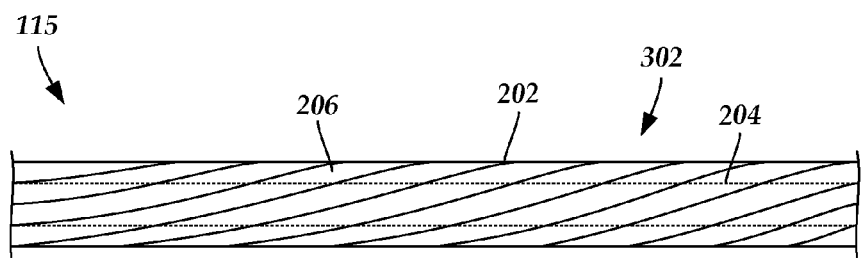
FIG. 3A is a schematic side view of one embodiment of a helical section of the multi-lumen conductor guide of FIG. 2A, the helical section defining a plurality of conductor lumens each defining a clockwise helical pathway around at least a portion of a central lumen, according to the invention.
Figure 3B:
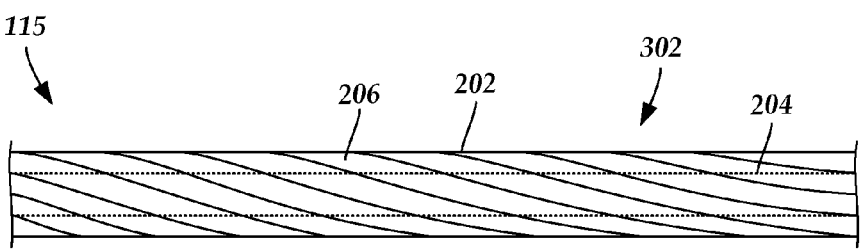
FIG. 3B is a schematic side view of another embodiment of a helical section of the multi-lumen conductor guide of FIG. 2A, the helical section defining a plurality of conductor lumens each defining a counter-clockwise helical pathway around at least a portion of a central lumen, according to the invention.

FIGS. 3A and 3B are schematic side views of two embodiments of a helical section 302 of the multi-lumen conductor guide 202. The helical section 302 can extend an entire length of the multi-lumen conductor guide 202, or extend along one or more portions thereof, where each helical section 302 is only part of the longitudinal length of the multi-lumen conductor guide 202. The conductor lumens 206 are twisted such that the individual conductor lumens 206 form helical pathways around the central lumen 204. The conductor lumens 206 can extend in either clockwise or counter-clockwise directions.

In FIG. 3A, the conductor lumens 206 are shown extending in a clockwise direction around to the central lumen 204 (e.g., the conductor lumens 206 wrap around the central lumen 204 in a clockwise direction when the multi-lumen conductor guide 202 is viewed from the distal end). In FIG. 3B, the conductor lumens 206 are shown extending in a counter-clockwise direction around to the central lumen 204 (e.g., the conductor lumens 206 wrap around the central lumen 204 in a counter-clockwise direction when the multi-lumen conductor guide 202 is viewed from the distal end).

The conductor lumens 206 of the helical section 302 can have any suitable pitch. The pitch can be either constant or variable. In some cases, the pitch may be at least 0.04 turns (i.e., 0.04 revolutions around a circumference of the central lumen 204) per cm. In some cases, the pitch may be no less than 0.1 turns per cm. In some cases, the pitch may be at least 0.2 turns per cm. In some cases, the pitch may be at least 0.25 turns per cm. In some cases, the pitch may be at least 0.8 turns per cm.

In some cases, the pitch may be at least 0.04 turns per cm and no greater than 0.8 turns per cm. In some cases, the pitch may be at least 0.1 turns per cm and no greater than 0.6 turns per cm. In some cases, the pitch may be at least 0.1 turns per cm and no greater than 0.4 turns per cm. In some cases, the pitch may be at least 0.2 turns per cm and no greater than 0.4 turns per cm. In some cases, the pitch may be approximately 0.3 turns per cm.

In some cases, for a 40 cm section of the multi-lumen conductor guide 202, each conductor lumen 206 of the helical section 302 forms at least 2, 3, 4, or 5 turns. In some cases, for a 40 cm section of the multi-lumen conductor guide 202, each conductor lumen 206 of the helical section 302 forms no more than 25 turns.

In some cases, for a 40 cm section of the multi-lumen conductor guide 202, each conductor lumen 206 of the helical section 302 forms at least 2 turns and no more than 15 turns. In some cases, for a 40 cm section of the multi-lumen conductor guide 202, each conductor lumen 206 of the helical section 302 forms no less than 3 turns and no more than 15 turns. In some cases, for a 40 cm section of the multi-lumen conductor guide 202, each conductor lumen 206 of the helical section 302 forms at least 4 turns and no more than 15 turns. In some cases, for a 40 cm section of the multi-lumen conductor guide 202, each conductor lumen 206 of the helical section 302 forms at least 5 turns and no more than 15 turns.

The conductor lumens 206 of the helical section 302 can be configured into any suitable arrangement. As shown in FIG. 2A and FIG. 2B, the helical section 302 may include a single layer of conductor lumens 206 disposed over the central lumen 204. Alternately, the helical section 302 may include two or more layers of conductor lumens 206 disposed over the central lumen 204. As shown in FIG. 2A and FIG. 2B, the conductor lumens 206 may be disposed over a single central lumen 204. Alternately, the conductor lumens 206 may be disposed over multiple central lumens 204.

In some cases, the helical section 302 extends along an entire length of the lead body 115 between, but excluding, the sections containing the electrodes (125 in FIG. 1) and the terminals (135 in FIG. 1). In other cases, the helical section 302 extends along one or more discrete sections of the lead body 115. When the helical section 302 extends along one or more discrete sections of the lead body 115, the discrete helical section 302 can be any suitable length. In some cases, the discrete helical section 302 is at least 1 cm, 2 cm, 3 cm, 4 cm, 5 cm, 6 cm, 7 cm, 8 cm, 9 cm, 10 cm, 15 cm, 20 cm, 25 cm, 30 cm, or longer.

In at least some embodiments, the plurality of conductor lumens 206 are encapsulated by the multi-lumen conductor guide 202 such that the conductor lumens 206 do not extend to an outer surface 222 of the multi-lumen conductor guide 202. In which case, when the conductors 208 are disposed in the conductor lumens 206, the conductors 208 are not exposed along the outer surface 222 of the multi-lumen conductor guide 202.

The central lumen 204 and the plurality of conductor lumens 206 can be arranged in any suitable manner. In preferred embodiments, the conductor lumens 206 are disposed in the multi-lumen conductor guide 202 such that the conductor lumens 206 are peripheral to the central lumen 204. Optionally, the lead body 115 may include one or more outer coatings of material 224 disposed over the outer surface 222 of multi-lumen conductor guide 202. In at least some embodiments, the one or more outer coatings 224 provide the lead body 115 with an isodiametric outer surface 226. It will be understood that the lead body 115 may be isodiametric either with or without application of one or more coatings 224.

In at least some embodiments, at least one of the conductor lumens 206 is configured and arranged to concurrently receive two or more conductors 208. In some embodiments, at least one of the conductor lumens 206 can be configured and arranged to receive a different number of conductors than at least one other of the conductor lumens 206. When the conductor lumens 206 are configured and arranged to receive a plurality of conductors, the conductor lumens 206 can be arranged in any suitable configuration.

When the helical section 302 extends along a discrete section of the multi-lumen conductor guide 202, the discrete helical section 302 can be disposed at any suitable location along the length of the lead body 115. In some cases, the discrete helical section 300 may abut the electrodes (125 in FIG. 1), the terminals (135 in FIG. 1), or both. In other cases, the discrete helical section 302 can be disposed somewhere along the length of the lead body 115 between the electrodes (125 in FIG. 1) and the terminals (135 in FIG. 1). When the discrete helical section 302 is disposed somewhere along the length of the lead body 115 between the electrodes (125 in FIG. 1) and the terminals (135 in FIG. 1), the remaining portions of the conductor lumens 206 can be arranged into one or more other configurations, such as a substantially-straight configuration (e.g., the conductor lumens 206 extend less than one revolution about a circumference of the central lumen 204 along a 20 cm length of the multi-lumen conductor guide 202).

The multi-lumen conductor guide 202 can be formed as a single-piece component or as a multi-piece component. The multi-lumen conductor guide 202 can be formed from any suitable material(s). For example, the multi-lumen conductor guide 202 can be formed from one or more thermoset polymers (e.g., silicone, or the like), thermoplastic polymers (e.g., polyurethane, or the like), or the like or combinations thereof.

The multi-lumen conductor guide 202 can be formed in any suitable manner. For example, the multi-lumen conductor guide 202 can be extruded. In some cases, the multi-lumen conductor guide 202 can be twisted as the multi-lumen conductor guide 202 is being extruded, or after extrusion.

The helical section(s) 3002 of the multi-lumen conductor guide 202 can be formed in any suitable manner. In some cases, the multi-lumen conductor guide 202 (or one or more portions thereof) is formed in a substantially-straight conductor-lumen configuration and then twisted, as desired, to form the one or more helical sections 302. Once the twisting is complete, the twisted multi-lumen conductor guide 202 may be heated to set the helical section(s). In other cases, the multi-lumen conductor guide 202 may be heated prior to twisting. In yet other cases, the multi-lumen conductor guide 202 may be heated while being twisted. The heating can be performed using at least one of: one or more transverse heating elements which heat one or more particular portions of the multi-lumen conductor guide 202 at a time, or an elongated heating element that heats the entire multi-lumen conductor guide 202 at once. In some instances, the lead body 115 can be heated from the inside out, for example, by using one or more heating elements disposed in the central lumen 204.

The electrodes 125 are coupled to one end of the multi-lumen conductor guide 202 and the terminals 135 are coupled to the opposing end of the multi-lumen conductor guide 202. In at least some embodiments, outer portions of the multi-lumen conductor guide 202 are ablated at the ends to expose the conductor lumens 206. In which case, the electrodes 125 may be disposed over the ablated portion at one end of the multi-lumen conductor guide 202, and the terminals 135 may be disposed over the ablated portion at the opposing end of the multi-lumen conductor guide 202 and be electrically coupled to conductors 208 extending within the exposed conductor lumens 206. In at least some embodiments, spacers are used to separate adjacent electrodes 125 (and adjacent terminals 135) from one another. In at least some embodiments, the spacers are isodiametric with the electrodes 125 (and terminals 135). In at least some embodiments, the lead body 115, the spacers, the electrodes 125, and the terminals 135 are isodiametric with one another.

Figure 4:
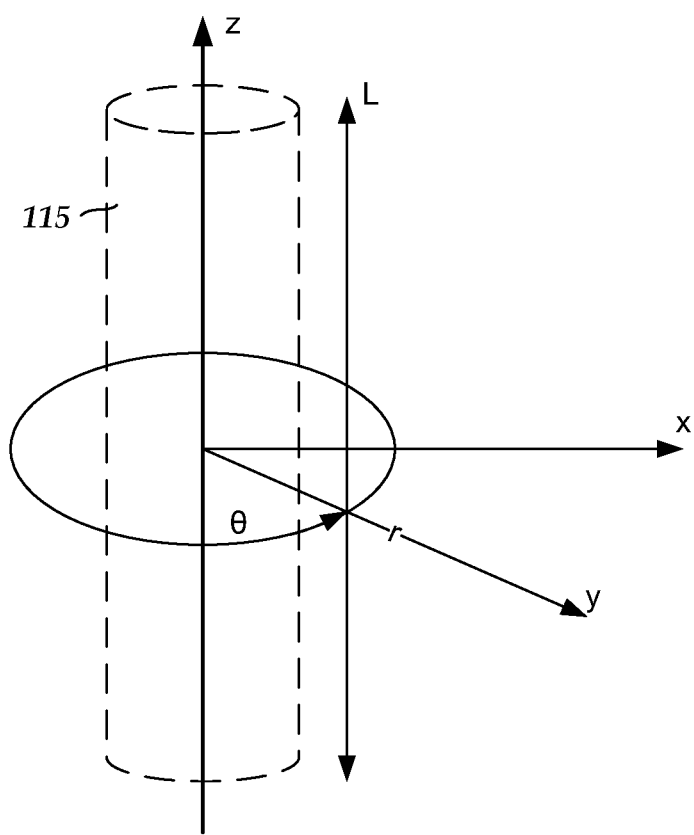
FIG. 4 is a schematic diagram of one embodiment of radial current steering along various electrodes disposed along the longitudinal length of the lead body of FIG. 1, according to the invention.

Turning to FIG. 4, it may be advantageous to stimulate patient tissue using segmented electrodes disposed around the circumference of the lead. Such electrodes enable directed stimulation (e.g., current steering), where stimulation energy is directed to discrete regions of patient tissue adjacent to the lead, while not stimulating other regions of adjacent patient tissue. In some instances, it may be desirable to stimulate a specific region of patient tissue ("a target stimulation region") disposed around the circumference of the lead without undesirably stimulating other patient tissue disposed about the circumference of the lead. In which case, the targeted stimulation region can be stimulated by rotating the lead until the directed stimulation energy propagating from one or more of the segmented electrodes is directed to the target stimulation region.

FIG. 4 is a schematic diagram to illustrate radial current steering along electrodes disposed along the longitudinal length of the lead body 115. While conventional lead configurations with ring electrodes are only able to steer current along the length of the lead (the z-axis), the segmented electrode configuration is capable of steering current in the x-axis, y-axis, as well as the z-axis. Thus, the centroid of stimulation may be steered in any direction in the three-dimensional space surrounding the lead body 115. In some embodiments, the radial distance, r, and the angle θ around the circumference of the lead body 115 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes enables the centroid of stimulation to be shifted to a variety of different locations along the lead body 115.

Figure 5:
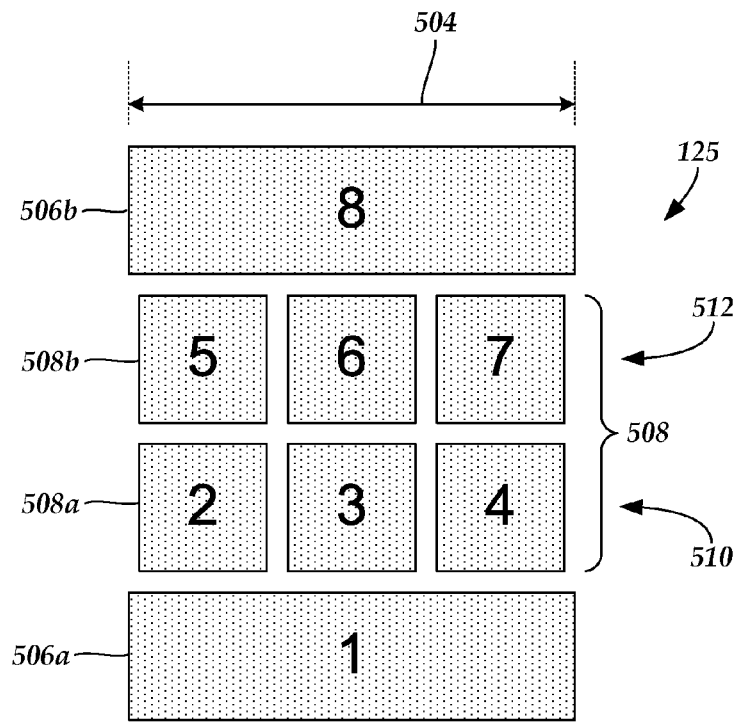
FIG. 5 is a schematic side view of one embodiment of the electrodes of FIG. 1 arranged into a flat configuration, according to the invention.

Turning to FIG. 5, the stimulation electrodes 125 may be disposed on the lead 100 in any suitable configuration. FIG. 5 illustrates one embodiment of the electrodes 125 unrolled from a cylindrical shape (see e.g., FIG. 1) so that the electrodes 125 are laid out flat, for clarity of illustration of the configuration of the electrodes. In other words, FIG. 5 is a two-dimensional version of the three-dimensional electrode configuration of FIG. 1.

In FIG. 5, the electrodes 125 are shown flattened such that the length indicated by arrow 504 is equal to the circumference of the lead body 115 (see e.g., FIG. 1). The electrodes 125 of FIG. 5 include two ring electrodes 506a and 506b flanking a plurality of segmented electrodes 508, such as segmented electrodes 508a and 508b arranged into two sets, or levels 510 and 512. The electrodes 125 may include any number of ring electrodes, or even a single ring electrode. For example, the electrodes 125 may include one ring electrode, two ring electrodes, three ring electrodes or four ring electrodes. In some embodiments, the electrodes 502 include five, six, seven or eight ring electrodes.

In at least some embodiments, the ring electrodes 506a, 506b are substantially cylindrical and wrap around an entire circumference of the lead body 115. In at least some embodiments, the outer diameter of the ring electrodes 506a, 506b is substantially equal to the outer diameter of the lead body. Furthermore, the width of ring electrodes 506a, 506b may vary according to the desired treatment and the location of the target neurons. In some embodiments the width of the ring electrode 506a is less than or equal to the diameter of the ring electrode 506b. In other embodiments, the width of the ring electrode 506a is greater than the diameter of the ring electrode 506b.

The electrodes 125 also include the segmented electrodes 508. The electrodes 125 may include any number of segmented electrodes 508 collectively wrapped around the circumference of the lead body 115. In some embodiments, the segmented electrodes 508 are grouped into sets of segmented electrodes, such as sets 510 and 512, where each set is configured for disposing around the circumference of the lead body 115 at or near a particular longitudinal position.

The electrodes 125 may include any number of sets of segmented electrodes 508. In at least some embodiments, the electrodes 125 include one, two, three, four, five, six, seven, eight, or more sets of segmented electrodes 508. In at least some embodiments, each set of segmented electrodes contains the same number of segmented electrodes 508. In some embodiments, each set of segmented electrodes contains three segmented electrodes 508. In at least some other embodiments, each set of segmented electrodes contains two, four, five, six, seven or eight segmented electrodes 508. The segmented electrodes 508 may vary in size and shape. In some embodiments, the segmented electrodes 508 are all of the same size, shape, diameter, width, area or any combination thereof.

Any combination of ring electrodes 506a, 506b and segmented electrodes 508 may be disposed on the lead body 115. For example, in FIG. 5 the lead body 115 includes the ring electrode 506a, two sets of segmented electrodes; each set formed of three segmented electrodes 508, and the ring electrode 506b. This configuration may simply be referred to as a 1-3-3-1 configuration. It may be useful to refer to the electrodes 125 with this shorthand notation. Other eight-electrode configurations include, for example, a 2-2-2-2 configuration, where four sets of segmented electrodes 508 are disposed on the lead, and a 4-4 configuration, where two sets of segmented electrodes, each having four segmented electrodes 508, are disposed on the lead. In some embodiments, the lead upon which the electrodes are disposed includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

In at least some embodiments, each set of segmented electrodes 508 may be disposed around the circumference of the lead body 115 to form a substantially or approximately cylindrical shape around the lead body 115. The spacing of the segmented electrodes 508 around the circumference of the lead body 115 may vary. In at least some embodiments, equal spaces, gaps, or cutouts are disposed between each segmented electrode 508 disposed around the circumference of the lead body 115 (i.e., each segmented electrode 508 within a given set). In other embodiments, the spaces, gaps, or cutouts between segmented electrodes 508 may differ in size or shape. In other embodiments, the spaces, gaps, or cutouts between segmented electrodes 508 may be uniform for a particular set of segmented electrodes 508 or for all sets of segmented electrodes 508.

When the segmented electrodes 508 are disposed on the lead body 115, the segmented electrodes 508 may be positioned in irregular or regular intervals around the circumference of the lead body 115 such that each of the different segmented electrodes 508 extends around a different portion of the circumference. When the segmented electrodes 508 are disposed on the lead body 115, for example in a 1-3-3-1 configuration, each of the segmented electrodes 508 extends partially around the circumference of the lead body 115 such that the segmented electrodes collectively extend no more than 98%, 96%, 94%, 92%, 90%, 80%, 70%, 60%, 50%, 40%, 30%, or 20% around the circumference of the lead body 115.

Turning briefly back to FIG. 4, the centroid of stimulation can be shifted within each set 510, 512 along the length of the lead body 115. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead body 115). In at least some other embodiments, each set of segmented electrodes is controlled independently. It will be understood that different stimulation profiles may be produced by varying the number of segmented electrodes within each set 510. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Regardless of the type of electrodes used, proper placement of the lead may be important in providing proper and adequate treatment. For example, in some cases the target stimulation region may be located on one side of a plane extending through the longitudinal length of the lead. In other cases, the target stimulation region may be located at a plane that is offset at some angle from the longitudinal length of the lead. Thus, it is desirable to be able to rotate the lead such that the appropriate one or more electrodes are in rotational alignment with the target stimulation region. It may, accordingly, be advantageous to be able to determine the circumferential position of the electrodes on the lead within the brain.

Turning back to FIG. 5, the electrodes 125 are shown numbered from 1 to 8. In at least some embodiments, when the electrodes 125 are disposed on the lead body 115 (see e.g., FIG. 1), each of the electrodes 125 is coupled to a different terminal of the plurality of terminals 135. In which case, for example, the ring electrode 506a, which is numbered "1," may be electrically coupled a particular terminal of the plurality of terminals 135. Similarly, the ring electrode 506b, which is numbered "8," may be electrically coupled a different particular terminal of the plurality of terminals 135. Likewise, each of the segmented electrodes 508 may be electrically coupled to a different terminal of the plurality of terminals 135.

In at least some embodiments, the terminals 135 are also numbered to correspond to particular electrodes 125. For example, in at least some embodiments the terminals are numbered 1-8 such that the proximal-most terminal of the plurality of terminals is numbered "1," and the next most proximal terminal is numbered "2," and so on. In at least some embodiments, the electrode "1" electrically couples with the terminal "1," the electrode "2" electrically couples with the terminal "2," and so on.

In at least some embodiments, the electrodes 125 are arranged such that when the electrodes 125 are disposed on the lead body (see e.g., FIG. 1), some of the segmented electrodes 508 align with one another along a longitudinal length of the lead body 115. For example, when the electrodes 125 are disposed on the lead body 115, the segmented electrode labeled "2" aligns along the longitudinal length of the lead body 115 with the segmented electrode labeled "5." Similarly, the segmented electrode labeled "3" aligns with the segmented electrode labeled "6," and the segmented electrode labeled "4" aligns with the segmented electrode labeled "7."

Figure 6:
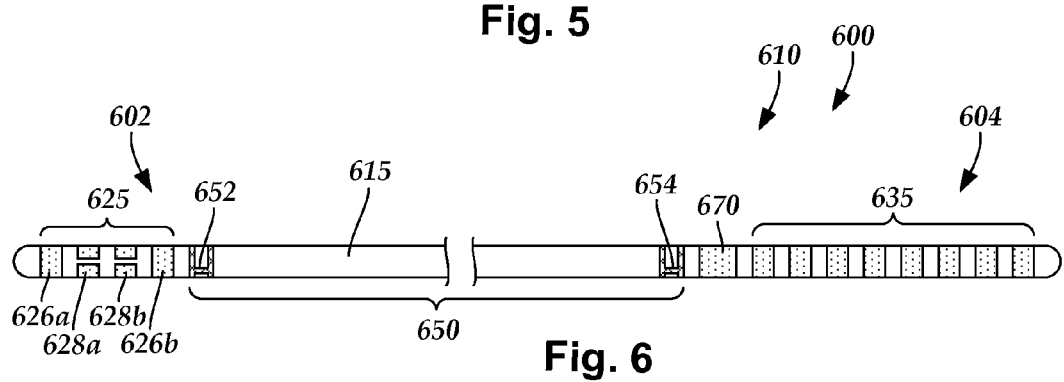
FIG. 6 is a schematic side view of one embodiment of a lead with segmented electrodes disposed at a distal end of the lead, terminals disposed at a proximal end of the lead, a distal marker rotationally aligned with at least one of the segmented electrodes, and a proximal marker rotationally aligned with the distal marker, according to the invention.

Turning to FIG. 6, during implantation of the lead, the distal end may be inserted into the patient while the proximal end of the lead is temporarily disposed external to the patient. During this time, a medical practitioner may position the distal end of the lead. During positioning of the distal end of the lead, the medical practitioner may rotate the lead to ensure alignment of one or more specific segmented electrodes with the target stimulation location. Rotation may be performed using the proximal end of the lead. Thus, it may be advantageous to enable the circumferential positioning of at least one of the plurality of segmented electrodes to be identified from the proximal end of the lead.

One way to identify the circumferential positioning of at least one of the plurality of segmented electrodes from the proximal end of the lead is to use one or more markers that align with the segmented electrodes and that extend along the longitudinal length of the lead body to the proximal end of the lead. Examples of lead bodies with markers extending along the lead body are found in, for example, U.S. Patent Application Ser. No. 61/364,960, which is incorporated herein by reference in its entirety. In some instances, however, placing markers along the longitudinal length of the lead may be difficult. For example, when the lead body includes twisted conductor lumens, such as when the lead body 115 includes a multi-lumen conductor guide 202 with one or more helical sections 302 (see e.g., FIGS. 2A-3B), it may be difficult to reliably extend the one or more markers along the longitudinal length of the lead body and accurately indicate, at the proximal end of the lead, the position of a particular electrode or electrodes.

As herein described, a lead assembly includes a marking arrangement configured to identify the circumferential position of at least one of the plurality of segmented electrodes disposed along the circumference of the lead body. Thus, when the lead is disposed in a patient the medical practitioner can determine the circumferential position of at least one of the plurality of segmented electrodes relative to the surroundings (e.g., the tissue of the brain) by observing the position of the marking arrangement. Observation of the marking arrangement can be by any suitable technique including, for example, visual observation, radiographic observation, spectroscopic observation, or the like or combinations thereof.

In at least some embodiments, the marking arrangement is configured to enable the medical practitioner to determine which of the one or more terminals are electrically coupled to the one or more identified segmented electrodes without relying on electrical testing, such as by using a multimeter. In at least some embodiments, the marking arrangement is configured to enable the circumferential positioning of at least one of the plurality of segmented electrodes to be identified when the lead body includes twisted conductor lumens, such as when the lead body 115 includes a multi-lumen conductor guide 202 with one or more helical sections 302 (see e.g., FIGS. 2A-3B).

In at least some embodiments, the marking arrangement includes one or more markers disposed along the distal end of the lead and one or more markers disposed along the proximal end of the lead body. In at least some embodiments, the one or more markers disposed along the distal end of the lead are discontinuous with the one or more markers disposed along the proximal end of the lead body. In at least some embodiments, neither the one or more markers disposed along the distal end of the lead, nor the one or more markers disposed along the proximal end of the lead body, are disposed directly on or in the lead body. In at least some embodiments, the one or more markers are disposed on or in, for example, one or more spacers disposed along the proximal or distal end of the lead body, one or more ring electrodes disposed along the distal end of the lead body, on the retention sleeve disposed along the proximal end of the lead body, or the like.

FIG. 6 is a schematic side view of one embodiment of a lead assembly 600 that includes a lead 610 with a lead body 615. A plurality of electrodes 625 are disposed along a distal end 602 of the lead body 615 and a plurality of terminals 635 are disposed along a proximal end 604 of the lead body 615. In at least some embodiments, a retention sleeve 670 is disposed along the proximal end 604 of the lead body 615 to facilitate retention of the proximal end 604 of the lead body 610 in a connector (see e.g., connector 170 of FIG. 1) during (and following) implantation.

The plurality of electrodes 625 are arranged into a configuration that is similar to the electrodes 125 of FIG. 5, and that include ring electrodes 626a and 626b, and segmented electrodes, such as segmented electrodes 628a and 628b. In FIG. 6 (and in other figures) the segmented electrodes 628a and 628b are aligned with one another along a longitudinal length of the lead body 615. Referring back to the numbering of the electrodes 125 of FIG. 5, the electrodes 628a and 628b may correspond, for example, to segmented electrodes "2" and "5." In alternate embodiments, the distal marker can be aligned with segmented electrodes "3" and "6," or "4" and "7."

A marking arrangement 650 is disposed on the lead body 615. In FIG. 6, the marking arrangement 650 includes a distal marker 652 disposed at the distal end 602 of the lead body 615 and a proximal marker 654 disposed at the proximal end 604 of the lead body 615. The distal marker 652 is configured to identify the circumferential position of one or more of the segmented electrodes along the circumference of the lead body 615. In FIG. 6, the distal marker 652 identifies the position of the segmented electrodes 628a and 628b. The proximal marker 654 is positioned such that the proximal marker 654 is rotationally aligned with the distal marker 652 along the longitudinal length of the lead body 615.

Thus when, for example, the distal marker 652 is aligned with segmented electrodes "2" and "5," the medical practitioner can identify the circumferential position of the segmented electrodes "2" and "5" by observing the proximal marker 654. Moreover, in at least some embodiments the medical practitioner can identify which terminals 635 correspond to (e.g., which terminals are electrically coupled to) the identified electrodes. In some embodiments, the markers 652, 654 are fixed in position. In alternate embodiments, the markers 652, 654 are rotatable around the circumference of the lead body 615. For example, in at least some embodiments when the distal marker 652 is aligned with the segmented electrodes "2" and "5," the distal marker 652 can be rotated to align with the segmented electrodes "3" and "6." In which case, the proximal marker 654 may also be rotatable to maintain alignment with the distal marker 652. In at least some embodiments, the markers 652, 654 can be fixed after rotating to the desired orientation.

The markers 652, 654 can be implemented in any suitable manner. In at least some embodiments, the markers 652, 654 are disposed on or in spacers disposed along either end of the lead body 615. In at least some embodiments, the distal marker 652 is disposed on or in a spacer disposed along the distal end of the lead body 615 such that the distal marker 652 is disposed proximal to the electrodes 625. In at least some embodiments, the distal marker 652 is disposed on or in a spacer disposed between two adjacent electrodes of the plurality of electrodes 625. In at least some embodiments, the proximal marker 654 is disposed on or in a spacer disposed along the proximal end of the lead body 615 such that the proximal marker 654 is disposed distal to the terminals 635. In at least some embodiments, the proximal marker 654 is disposed between two adjacent terminals of the plurality of terminals 635.

In at least some embodiments, at least one of the markers 652, 654 includes a radiopaque material. It may be advantageous to use at least one radiopaque marker to enable visualization of the circumferential positioning of at least one of the plurality of electrodes 625 through visual inspection or radiological methods. In some embodiments, the radiopaque material includes barium sulfate. In some embodiments, the radiopaque material includes titanium dioxide. In at least some embodiments, one or more of the markers 652, 654 include a metallic element that is disposed onto or into the lead body 615. Materials for the metallic element include, for example, biocompatible materials, such as platinum, platinum iridium, stainless steel, titanium, and the like.

In at least some embodiments, the marking arrangement 650 includes a plurality of distal markers 652, or a plurality of proximal markers 654, or a plurality of both distal markers 652 and proximal markers 654. In which case, each of the distal markers 652 may be distinguishable from one another, and each of the proximal markers 654 may be distinguishable from one another. In some instances, when the marking arrangement 650 includes a plurality of distal markers 652, each of the distal markers 652 may align with a different segmented electrode or group of longitudinally-aligned segmented electrodes.

When multiple distal markers 652, proximal markers 654, or both, are used, the different markers may be distinct from one another. For example, when multiple distal markers 652 are used, one or more of the distal markers 652 may be formed from a color that is different from at least one other of the distal markers 652. In at least some embodiments, at least one of the distal markers 652 may be a different shade of the same color from at least one other of the distal markers 652. For example, a first distal marker 652 may be a particular color, while second and third distal markers 652 are progressively darker shades of the same color. Alternatively, the distal markers 652 may be of different widths. In some embodiments, the distal markers 652 may begin with a single thin distal marker 652, with successive distal markers 652 progressively increasing in width around the perimeter of the lead body. Any combination of thin and wide distal markers 652 is possible. Additionally, the distal markers 652 may also be of different textures or configurations. Any configuration of the distal markers 652 may be utilized, so long as they are able to denote a specific circumferential position. Alternatively, the distal markers 652 may have different radiographic properties; for example, some distal markers 652 may appear darker than others when imaged. It will be understood that the same techniques can be used to distinguish multiple proximal markers 654 from one another.

In at least some embodiments, the markers 652, 654 each extend along the longitudinal length of the lead body 115. The markers 652, 654 can extend any suitable length along the longitudinal length of the lead body 115. In at least some embodiments, the markers 652, 654 extend no more than 30 mm, 25 mm, 20 mm, 15 mm, 10 mm, 9 mm, 8 mm, 7 mm, 6 mm, 5 mm, 4 mm, 3 mm, 2 mm, 1 mm, or less along the longitudinal length of the lead body 115.

Figure 7:
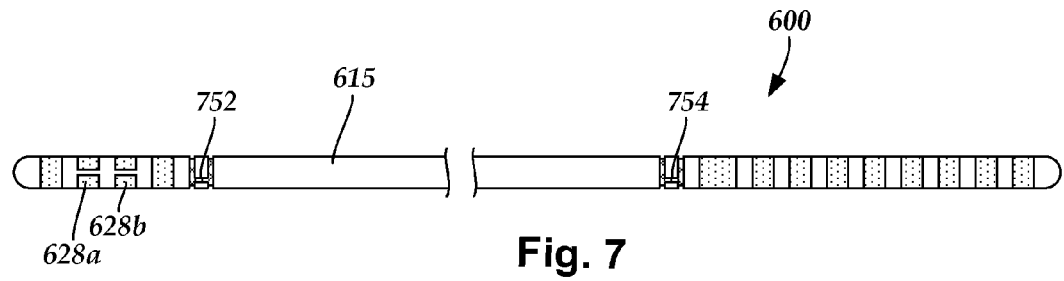
FIG. 7 is a schematic side view of another embodiment of a distal marker disposed at a distal end of the lead of FIG. 6 and a proximal marker disposed at a proximal end of the lead of FIG. 6, where the distal and proximal markers are inset from an outer surface of the lead, according to the invention.

In at least some embodiments, the markers are isodiametric with the lead body, the electrodes, and the terminals. In alternate embodiments, at least one of the markers is inset from remaining portions of the lead body. FIG. 7 is a schematic side view of another embodiment of the lead assembly 600. In FIG. 7, the lead assembly 600 includes a distal marker 752 and a proximal marker 754 that are both inset from the lead body 615. In FIG. 7, the distal marker 752 is disposed on the lead body 615 such that the distal marker 752 is aligned with the segmented electrodes 628a and 628b along the longitudinal length of the lead body 615. The proximal marker 754 is aligned with the distal marker 752 along the longitudinal length of the lead body 615.

Figure 8A:
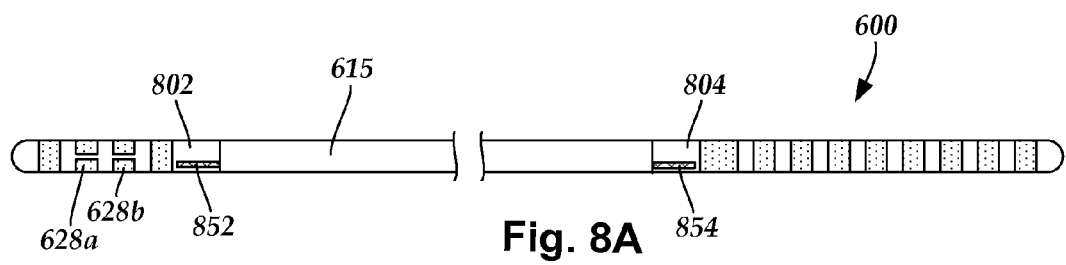
FIG. 8A is a schematic side view of another embodiment of a distal marker disposed at a distal end of the lead of FIG. 6 and a proximal marker disposed at a proximal end of the lead of FIG. 6, where the distal and proximal markers are formed on or in spacers, according to the invention.
Figure 8B:
FIG. 8B is a schematic side view of another embodiment of a distal marker disposed at a distal end of the lead of FIG. 6 and a proximal marker disposed at a proximal end of the lead of FIG. 6, where the distal and proximal markers are formed on or in spacers, according to the invention.

The markers may be formed from either multiple elements or single elements. FIG. 8A and FIG. 8B are schematic side views of another embodiment of the lead assembly 600. In FIG. 8A and FIG. 8B, the lead assembly 600 includes a distal marker 852 formed as a single element disposed on or in a spacer 802 disposed along the distal end of the lead body. Similarly, the lead assembly 600 includes a proximal marker 854 formed as a single element disposed on or in a spacer 804 disposed along the proximal end of the lead body. In alternate embodiments, at least one of the distal marker 852 or the proximal marker 854 includes multiple elements disposed on or in a spacer disposed along the lead body.

In FIG. 8A, the distal marker 852 is disposed on or in a distal spacer 802 disposed proximal to the electrodes 625, and the proximal marker 854 is disposed on or in a proximal spacer 804 disposed distal to the terminals 635. In FIG. 8B, the distal marker 852 is disposed on or in a distal spacer 802 disposed between two adjacent electrodes of the plurality of electrodes 625, and the proximal marker 854 is disposed on or in a proximal spacer 804 disposed between two adjacent terminals of the plurality of terminals 635.

In FIG. 8A and FIG. 8B, the distal spacer 802 is disposed along the lead body 615 such that the distal marker 852 is aligned with the segmented electrodes 628a and 628b along the longitudinal length of the lead body 615. The proximal spacer 804 is disposed along the lead body 615 such that the proximal marker 854 is aligned with the distal marker 852 along the longitudinal length of the lead body 615. In at least some embodiments, at least one of the distal marker 852 or the proximal marker 854 is disposed on or in multiple spacers disposed along the longitudinal length of the lead body 615.

Figure 9:
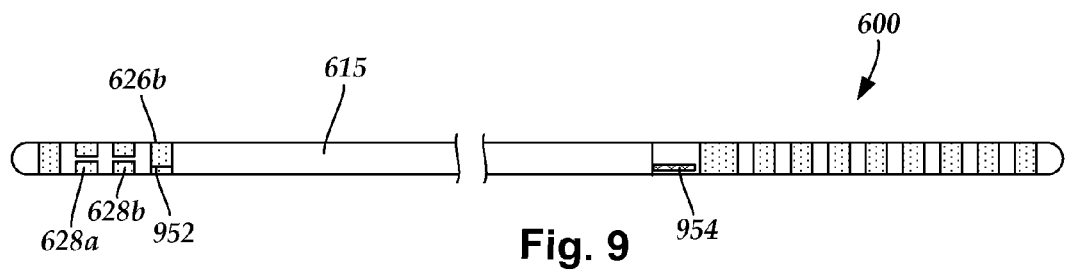
FIG. 9 is a schematic side view of another embodiment of a distal marker disposed at a distal end of the lead of FIG. 6 and a proximal marker disposed at a proximal end of the lead of FIG. 6, where the distal marker is formed on or in a ring electrode, according to the invention.

In at least some embodiments, the distal marker is disposed on or in one or more of the ring electrodes. FIG. 9 is a schematic side view of another embodiment of the lead assembly 600. In FIG. 9, the lead assembly 600 includes a distal marker 952 disposed on the ring electrode 626b. In at least some embodiments, the distal marker 952 is a distinct element (e.g., visually distinct, radiopaque, or the like or combinations thereof) disposed on or in the ring electrode 626b. In other embodiments, the ring electrode 626b is formed as an open loop, where the ring electrode 626b is C-shaped with a seam or strip of material extending along the longitudinal length of the lead body 615 and separating two opposing ends of the ring electrode 626b when the ring electrode 626b is wrapped around the lead body 615. In FIG. 9, the distal marker 952 is disposed on the ring electrodes 626b such that the distal marker 952 is aligned with the segmented electrodes 628a and 628b along the longitudinal length of the lead body 615. The proximal marker 954 is aligned with the distal marker 952 along the longitudinal length of the lead body 615.

Figure 10:
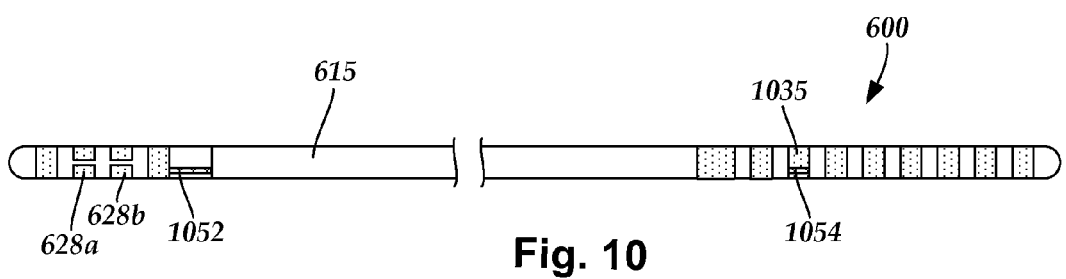
FIG. 10 is a schematic side view of an embodiment of a distal marker disposed at a distal end of the lead of FIG. 6 and a proximal marker disposed at a proximal end of the lead of FIG. 6, where the proximal marker is formed on or in a terminal, according to the invention.

In at least some embodiments, the proximal marker is disposed on or in one or more of the terminals. FIG. 10 is a schematic side view of another embodiment of the lead assembly 600. In FIG. 10, the lead assembly 600 includes a proximal marker 1054 disposed on a terminal 1035 of the plurality of terminals (635 in FIG. 6). In at least some embodiments, the proximal marker 1054 is a distinct element (e.g., visually distinct, radiopaque, or the like or combinations thereof) disposed on or in the terminal 1035. In other embodiments, the terminal 1035 is formed as an open loop, where the terminal 1035 is C-shaped with a seam or strip of material extending along the longitudinal length of the lead body 615 and separating two opposing ends of the terminal 1035 when the terminal 1035 is wrapped around the lead body 615. In FIG. 10, the proximal marker 1054 is disposed on the terminal 1035 such that the proximal marker 1054 is aligned with a distal marker 1052 which, in turn, is aligned with the segmented electrodes 628a and 628b along the longitudinal length of the lead body 615.

Figure 11:
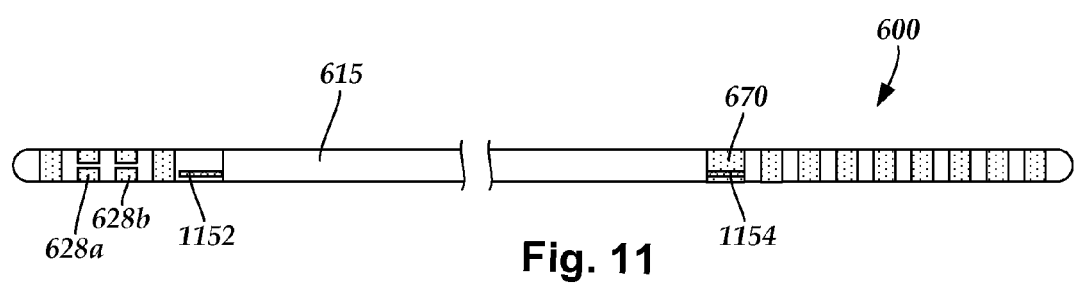
FIG. 11 is a schematic side view of another embodiment of a distal marker disposed at a distal end of the lead of FIG. 6 and a proximal marker disposed at a proximal end of the lead of FIG. 6, where the proximal marker is formed on or in a retention sleeve, according to the invention.

In at least some embodiments, the proximal marker is disposed on or in the retention sleeve. FIG. 11 is a schematic side view of another embodiment of the lead assembly 600. In FIG. 11, the lead assembly 600 includes a proximal marker 1154 disposed on or in the retention sleeve 670. In at least some embodiments, the proximal marker 1154 is a distinct element (e.g., visually distinct, radiopaque, or the like or combinations thereof) disposed on or in the retention sleeve 670. In other embodiments, the retention sleeve 670 is formed as an open loop, where the retention sleeve 670 is C-shaped with a seam or strip of material extending along the longitudinal length of the lead body 615 and separating two opposing ends of the retention sleeve 670 when the retention sleeve 670 is wrapped around the lead body 615. In FIG. 11, the proximal marker 1154 is disposed on the retention sleeve 670 such that the proximal marker 1154 is aligned with a distal marker 1152 which, in turn, is aligned with the segmented electrodes 628a and 628b along the longitudinal length of the lead body 615.

It will be understood that the marking arrangement may include any combination of the markers described above, with reference to FIGS. 6-11. For example, the distal marker may be disposed on or in one or more of the ring electrodes and the proximal marker may be disposed on or in the retention sleeve. It will also be understood that the properties of the markers discussed above, with reference to FIG. 6 apply equally to each of the embodiments of markers described above, with reference to FIGS. 7-11.

In each of the embodiments shown in FIGS. 6-11, the marking arrangement includes at least one proximal marker and at least one distal marker that are longitudinally aligned with one another that that are discontinuous with one another along the lead body. In each of the embodiments shown in FIGS. 6-11, the marking arrangement includes at least one proximal marker and at least one distal marker that are not disposed directly on or in the lead body. In alternate embodiments, the marking arrangement is formed as one or more ablations each extending along substantially entirely the longitudinal length of the lead body.

Figure 12:
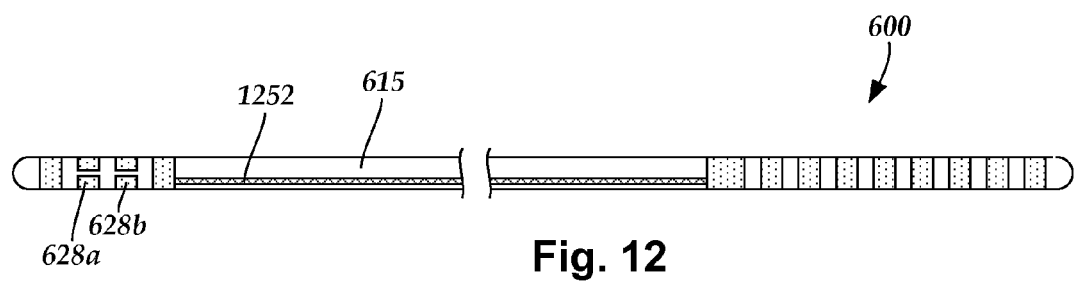
FIG. 12 is a schematic side view of another embodiment of a marker formed as an ablation extending along an entire length of the lead of FIG. 6, according to the invention.

FIG. 12 is a schematic side view of another embodiment of the lead assembly 600. The lead assembly 600 includes a marker 1252 formed as an ablation extending along the longitudinal length of the lead body 615. In FIG. 12, the marker 1252 is aligned with the segmented electrodes 628a and 628b along the longitudinal length of the lead body 615. In at least some embodiments, the ablation is formed along one or more outer layers (see e.g., 224 of FIG. 4A) of the lead body 615. The ablation 1252 can be formed in any suitable manner including, for example, laser ablation. In embodiments where the lead body 615 includes a multi-lumen conductor guide (202 in FIGS. 2A-2B) with one or more helical sections 302 (see e.g., FIGS. 2A-3B), the ablation 1252 is formed after the multi-lumen conductor guide 202 has been twisted.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead assembly for an electrical stimulation system, the lead assembly comprising:
   a lead body having a distal end, a proximal end, a longitudinal length, and a circumference;
   a multi-lumen conductor guide disposed along at least a portion of the longitudinal length of the lead body, the multi-lumen conductor guide having and outer surface and defining a central lumen and a plurality of conductor lumens disposed around the central lumen, wherein at least a portion of the multi-lumen conductor guide is twisted and forms at least one helical section with the plurality of conductor lumens forming helical pathways around the central lumen, and wherein the plurality of conductor lumens are encapsulated by the multi-lumen conductor guide such that the plurality of conductor lumens do not extend to the outer surface of the multi-lumen conductor guide;
   a plurality of electrodes disposed along the distal end of the lead body, the plurality of electrodes comprising a plurality of segmented electrodes, wherein each of the plurality of segmented electrodes extends partially around the circumference of the lead body;
   a plurality of terminals disposed along the proximal end of the lead body;
   a plurality of conductors electrically coupling at least one of the plurality of electrodes to at least one of the plurality of lead terminals;
   at least one distal marker formed as a strip extending along the distal end of the lead body, the distal marker identifying the circumferential position of at least one of the plurality of segmented electrodes along the lead body, wherein the distal marker is aligned with the at least one of the plurality of segmented electrodes along the longitudinal length of the lead body; and
   at least one proximal marker formed as a strip extending along the proximal end of the lead body, wherein the proximal marker is aligned with the distal marker along the longitudinal length of the lead body, and wherein the at least one proximal marker is disposed distal to at least one terminal of the plurality of terminals;
   wherein the at least one distal marker and the at least one proximal marker are discontinuous with one another along the lead body.

2. The lead assembly of claim 1, further comprising a retention sleeve disposed along the proximal end of the lead body, the retention sleeve configured and arranged for facilitating retention of the proximal end of the lead body in an implantable connector coupleable to the lead assembly.

3. The lead assembly of claim 2, wherein the at least one proximal marker is disposed in or on the retention sleeve.

4. The lead assembly of claim 1, wherein the at least one distal marker is disposed in or on a spacer disposed along the distal end of the lead body.

5. The lead assembly of claim 1, wherein the at least one proximal marker is disposed in or on a spacer disposed along the proximal end of the lead body.

6. The lead assembly of claim 1, wherein at least one of the at least one distal marker or the at least one proximal marker comprises at least one of a metallic material or a radiopaque material.

7. The lead assembly of claim 1, wherein the plurality of electrodes comprises at least one ring electrode.

8. The lead assembly of claim 7, wherein the at least one distal marker is disposed on or in the at least one ring electrode.

9. The lead assembly of claim 1, wherein the at least one proximal marker is disposed on or in at least one of the plurality of terminals.

10. The lead assembly of claim 1, wherein the lead body, the plurality of electrodes, the plurality of terminals, the at least one distal marker, and the at least one proximal marker are each isodiametric with one another.

11. The lead assembly of claim 1, wherein the lead body, the plurality of electrodes, and the plurality of terminals are each isodiametric with one another, and wherein the at least one distal marker and the at least one proximal marker each have outer diameters that are smaller than outer diameters of the lead body.

12. The lead assembly of claim 1, wherein the at least one distal marker comprises a plurality of distal markers, and wherein the plurality of distal markers are each distinct from one another by at least one of color, width, or texture.

13. The lead assembly of claim 1, wherein the at least one proximal marker comprises a plurality of proximal markers, and wherein the plurality of proximal markers are each distinct from one another by at least one of color, width, or texture.

14. The lead assembly of claim 1, wherein neither the at least one distal marker or the at least one proximal marker is disposed directly on or in the lead body.

15. A deep brain stimulation system comprising:
   the lead assembly of claim 1;
   a lead extension having a first end and an opposing second end, the lead extension configured and arranged to coupling with the lead body of the lead assembly, the lead extension comprising
      a plurality of lead extension terminals disposed on the second end of the lead extension;
      a connector disposed at the first end of the lead extension, the connector comprising a connector housing defining a connector port, the connector port configured and arranged to receive the lead body of the lead extension,
      a plurality of connector contacts disposed in the connector port, the connector contacts configured and arranged to electrically couple to the lead terminals when the lead body is received by the connector housing, and
      a plurality of conductors extending along a length of the lead extension, wherein each of the conductors electrically couples at least one of the lead extension terminals to at least one of the plurality of connector contacts; and
   a control unit coupleable to the second end of the lead extension, the control unit configured and arranged for providing stimulation to the plurality of electrodes of the lead assembly.

16. A method for implanting a lead into a brain of a patient, the method comprising:

inserting the lead assembly of claim 1 into a cranium of the patient with the distal end of the lead body inserted into the patient and the proximal end of the lead body extending outward from the patient;

rotating the lead body until a desired electrical stimulation is achieved by the plurality of segmented electrodes; and identifying the circumferential orientation of the plurality of segmented electrodes by observing the circumferential orientation of the at least one proximal marker.

17. A method for marking a lead of an implantable electrical stimulation system, the method comprising:

forming an elongated multi-lumen conductor guide defining a central lumen and a plurality of conductor lumens arranged around the central lumen;

twisting at least a portion of the multi-lumen conductor guide to form at least one helical section where the plurality of conductor lumens each forms a helical pathway around the central lumen;

inserting at least one conductor into one of the plurality of conductor lumens;

forming a plurality of segmented electrodes along one end of the multi-lumen conductor guide;

electrically coupling the plurality of segmented electrodes to the at least one conductor; and forming an ablation along a longitudinal length of the twisted multi-lumen conductor guide, wherein the ablation is aligned along the longitudinal length of the multi-lumen conductor guide with a one of the plurality of segmented electrodes.

18. The lead assembly of claim 1, wherein the at least one proximal member is disposed distal to each of the plurality of terminals.

19. The lead assembly of claim 1, wherein the at least one proximal member is disposed between two adjacent terminals of the plurality of terminals.

20. The lead assembly of claim 1, wherein the at least one distal member is disposed between two adjacent electrodes of the plurality of electrodes.

* * * * *